(12) United States Patent
Fruci et al.

(10) Patent No.: US 10,786,668 B2
(45) Date of Patent: Sep. 29, 2020

(54) PROTECTIVE SHEATH AND METHOD FOR PROTECTING A LEAD DURING IMPLANT AND PULSE GENERATOR REPLACEMENT

(71) Applicant: Cardiac Pacemakers, Inc., St. Paul, MN (US)

(72) Inventors: Angelo Fruci, Mahtomedi, MN (US); Arthur J. Foster, Blaine, MN (US)

(73) Assignee: Cardiac Pacemakers Inc., St Paul, MN (US)

( * ) Notice: Subject to any disclaimer, the term of this patent is extended or adjusted under 35 U.S.C. 154(b) by 350 days.

(21) Appl. No.: 15/702,449

(22) Filed: Sep. 12, 2017

(65) Prior Publication Data

US 2018/0071517 A1 Mar. 15, 2018

Related U.S. Application Data

(60) Provisional application No. 62/394,037, filed on Sep. 13, 2016.

(51) Int. Cl.
| | | |
|---|---|---|
| *A61N 1/05* | (2006.01) | |
| *A61M 25/00* | (2006.01) | |
| *A61B 17/34* | (2006.01) | |
| *A61B 46/17* | (2016.01) | |
| *A61B 46/10* | (2016.01) | |
| *A61N 1/36* | (2006.01) | |
| *A61M 25/06* | (2006.01) | |

(Continued)

(52) U.S. Cl.
CPC .......... *A61N 1/056* (2013.01); *A61B 17/3468* (2013.01); *A61B 46/10* (2016.02); *A61B 46/17* (2016.02); *A61M 25/0074* (2013.01); *A61B 17/3431* (2013.01); *A61B 2017/00991* (2013.01); *A61B 2017/320056* (2013.01); *A61M 25/0662* (2013.01); *A61M 2025/0079* (2013.01); *A61N 1/36* (2013.01)

(58) Field of Classification Search
CPC .......................... A61N 1/056; A61M 25/0074
USPC .......................................................... 607/122
See application file for complete search history.

(56) References Cited

U.S. PATENT DOCUMENTS

| | | | |
|---|---|---|---|
| 4,327,735 | A | 5/1982 | Hampson |
| 4,643,202 | A | 2/1987 | Roche |
| 5,054,821 | A | 10/1991 | Hillstead |

(Continued)

FOREIGN PATENT DOCUMENTS

WO 2011065991 A1 6/2011

OTHER PUBLICATIONS

H1465. Implantable Lead Infection Barrier. Jul. 4, 1995. Stokes, et. al. 4 pages.

*Primary Examiner* — Nadia A Mahmood
(74) *Attorney, Agent, or Firm* — Faegre Drinker Biddle & Reath LLP

(57) ABSTRACT

An introducer sheath assembly including an introducer sheath and a protective sheath. The introducer sheath includes a hub having a proximal end and a distal end, and a tubular sheath projecting from the distal end of the hub. The protective sheath has a proximal end and a distal end. The distal end of the protective sheath is attached to the hub adjacent to the proximal end of the hub. The protective sheath is configurable between an undeployed state wherein the proximal end of the protective sheath is adjacent to the hub, and a deployed state wherein the proximal end of the protective sheath is away from the hub.

20 Claims, 8 Drawing Sheets

(51) Int. Cl.
 *A61B 17/00* (2006.01)
 *A61B 17/32* (2006.01)

(56) References Cited

U.S. PATENT DOCUMENTS

| | | |
|---|---|---|
| 6,035,239 A | 3/2000 | Patag et al. |
| 6,324,414 B1 | 11/2001 | Gibbons et al. |
| 6,634,364 B2 * | 10/2003 | Westlund ............... A61N 1/056 |
| | | 128/898 |
| 6,669,980 B2 | 12/2003 | Hansen |
| 2009/0259283 A1 | 10/2009 | Brandt et al. |
| 2011/0125241 A1 | 5/2011 | Cobian et al. |
| 2012/0097176 A1 | 4/2012 | Pitaoulis |

* cited by examiner

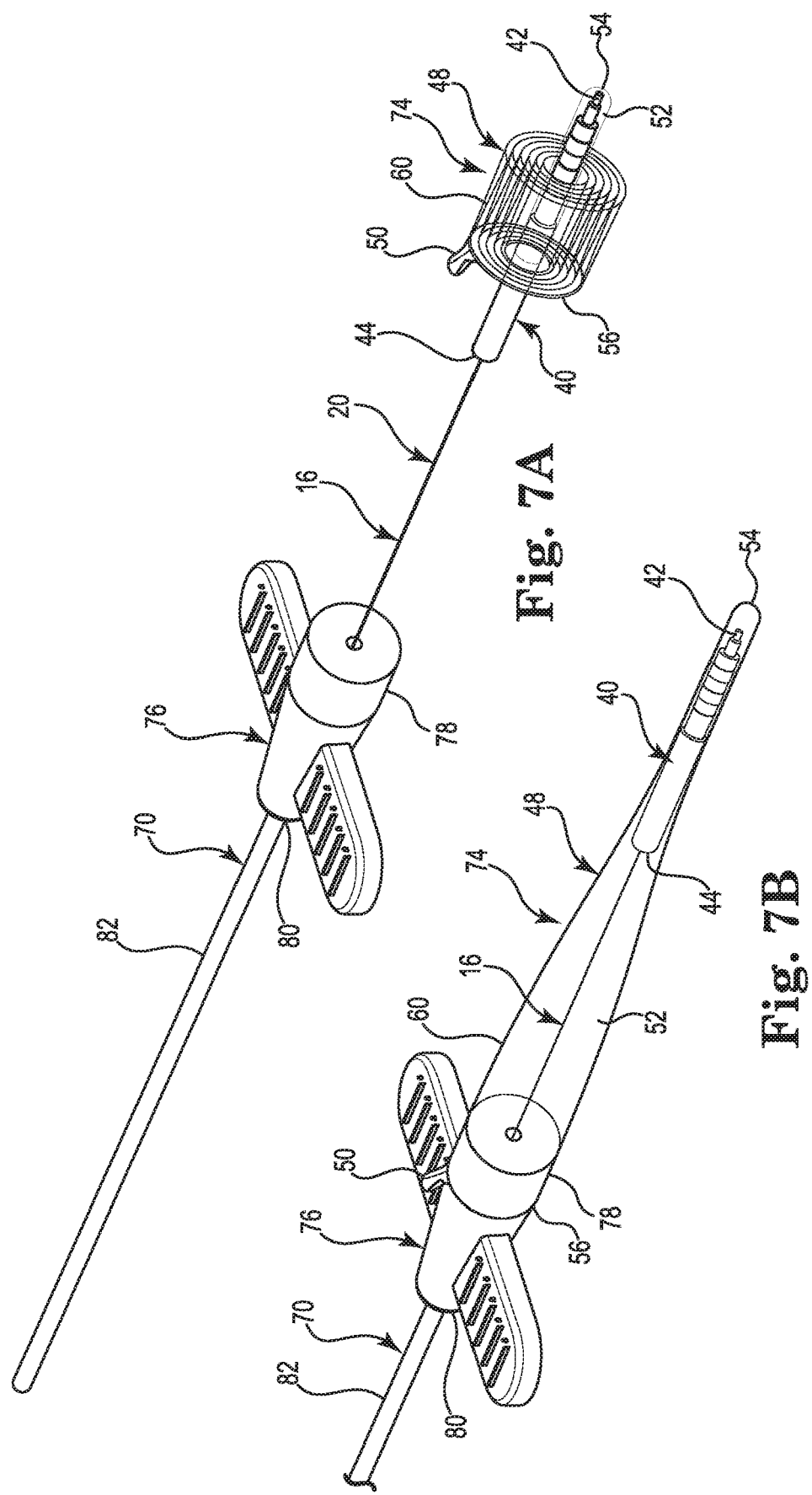

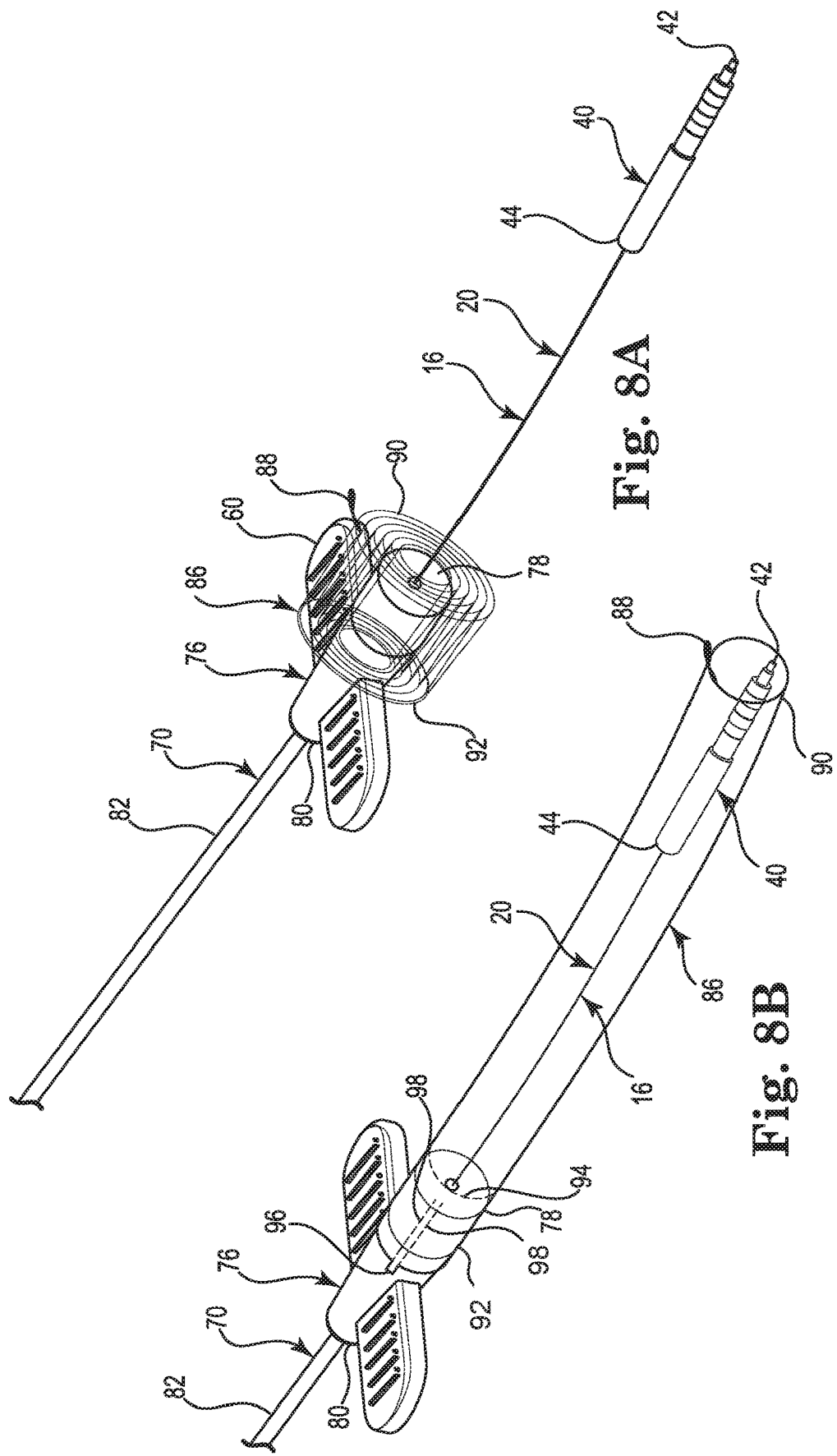

PROTECTIVE SHEATH AND METHOD FOR PROTECTING A LEAD DURING IMPLANT AND PULSE GENERATOR REPLACEMENT

CROSS-REFERENCE TO RELATED APPLICATION

This application claims priority to Provisional Application No. 62/394,037, filed Sep. 13, 2016, which is herein incorporated by reference in its entirety.

TECHNICAL FIELD

The present invention relates to implantable medical devices and methods for protecting implantable medical devices from bacterial contamination. More specifically, the invention relates to devices and methods for protecting implantable medical devices leads from bacterial contamination.

BACKGROUND

Medical devices may be implanted in a subcutaneous pocket to support sensing intrinsic physiological electrical activity, delivering a therapeutic stimulus to patient tissue, or providing other therapy to specific treatment sites. For example, a pulse generator may be implanted in a subcutaneous pocket in a patient's chest, with one or more electrical leads extending from the pulse generator to treatment sites within the patient.

Implantable medical device electrical leads may be subcutaneously implanted within a patient through the use of a tunneling tool. The tunneling tool typically includes an elongated tunneling rod or stylet inserted through a lumen of a splitable or peelable introducer sheath. The tip of the tunneling rod protrudes through the end of the introducer sheath as the tunneling rod and introducer sheath are inserted through an incision in a patient. The tapered tip of the tunneling rod eases the transit of the tunneling tool as the tunneling rod is driven to the desired location under the patient's skin. Once the tip of the tunneling rod is at the desired location, the tunneling rod is removed and the introducer sheath is left behind to provide a passageway for insertion of the lead through lumen of the introducer sheath to the implant location. Following insertion of the lead, the introducer sheath is extracted from the patient and the lead end is inserted into the subcutaneous pocket along with, for example, the pulse generator.

Implanting a medical device within a patient inherently exposes the patient to a risk of a nosocomial (e.g., hospital-acquired) infection associated with bacteria adhering to the exterior of the medical device. For example, the average nosocomial infection rate associated with the implantation of pacemakers and implantable cardioverter defibrillators is approximately three percent. In some cases of infection, the implantable medical device, including, for example, a pulse generator and electrical leads, must be completely removed. Following removal, the infection must be cured and the patient must heal enough to tolerate implantation of a replacement medical device. The costs of such infections are significant, not only intrinsically, but also in terms of the physical and emotional stress suffered by the patient.

Improved devices and methods are needed to help prevent subcutaneous pocket infections which may result from implanting a medical device within a patient.

SUMMARY

Example 1 is an introducer sheath assembly including an introducer sheath and a protective sheath. The introducer sheath includes a hub having a proximal end and a distal end, and a tubular sheath projecting from the distal end of the hub. The protective sheath has a proximal end and a distal end. The distal end of the protective sheath is attached to the hub adjacent to the proximal end of the hub. The protective sheath is configurable between an undeployed state wherein the proximal end of the protective sheath is adjacent to the hub and a deployed state wherein the proximal end of the protective sheath is away from the hub.

Example 2 is the introducer sheath assembly of Example 1, further including a tab projecting from the protective sheath at the proximal end of the protective sheath.

Example 3 is the introducer sheath assembly of either of Examples 1 and 2, wherein in the undeployed state, at least a portion of the protective sheath is folded by doubling the protective sheath back upon itself, and in the deployed state the protective sheath is unfolded.

Example 4 it the introducer sheath assembly of any of Example 1-3, wherein a diameter of the protective sheath in the deployed state is constant along its length.

Example 5 is the introducer sheath assembly of any of Examples 1-4, wherein the protective sheath is attached to the hub by a lap joint.

Example 6 is the introducer sheath assembly of any of Examples 1-5, wherein the protective sheath includes a scored portion adjacent to the hub.

Example 7 is a protective sheath configured to enclose a proximal end of an implantable medical electrical lead, the proximal end of the lead including a terminal pin and a portion of a lead projecting from a distal end of the terminal pin. The protective sheath includes a tubular a tubular body forming a lumen extending from a proximal end to a distal end of the tubular body. The lumen is open at the distal end of the tubular body. The tubular body includes a proximal section and a distal section. The proximal section is adjacent to the proximal end of the tubular body and configured to enclose within the lumen a proximal end of the terminal pin. The distal section extends from the proximal section to the distal end of the tubular body. The distal section is configurable between an undeployed state wherein the distal section encloses within the lumen at least a portion of the terminal pin distal from the proximal end of the terminal pin, and a deployed state wherein the distal section encloses within the lumen the portion of the terminal pin distal from the proximal end of the terminal pin and the portion of the lead projecting from the distal end of the terminal pin.

Example 8 is the protective sheath of Example 7, wherein the lumen has a diameter of about 0.2 mm to about 8.3 mm.

Example 9 is the protective sheath of either of Examples 7 or 8, wherein the lumen is closed at the proximal end of the tubular body.

Example 10 is the protective sheath of any of Examples 7-9, further including a tab projecting from the tubular body at the distal end of the tubular body.

Example 11 is the protective sheath of any of Example 7-10, wherein in the undeployed state, at least a portion of the distal section is folded by doubling the tubular body back upon itself, and in the deployed state at least a portion of the folded distal section is unfolded.

Example 12 is the protective sheath of any of Example 7-11, wherein the lumen at the distal end of the tubular body is configured to enclose a proximal end of an introducer sheath hub.

Example 13 is a method of protecting a proximal end of an implantable medical electrical lead from bacterial contamination while a distal end of the implantable medical electrical lead is implanted within a patient, the proximal end of the implantable medical electrical lead projecting from a proximal end of a hub of an introducer sheath. The method includes gripping a proximal end of an undeployed protective sheath attached to the proximal end of the hub by a distal end of the protective sheath, and deploying the protective sheath around the proximal end of the implantable medical electrical lead by pulling the proximal end of the protective sheath away from the hub until the proximal end of the protective sheath extends past a proximal end of the implantable medical electrical lead.

Example 14 is the method of Example 13, wherein before deploying, at least a portion of the protective sheath is folded by doubling the protective sheath back upon itself, and deploying the protective sheath unfolds the protective sheath.

Example 15 is the method of either of Examples 13 or 14, wherein gripping the proximal end of the undeployed protective sheath includes gripping a tab projecting from the proximal end of the protective sheath, and deploying the protective sheath includes pulling the tab past the end of the proximal end of the implantable medical electrical lead.

Example 16 is a protective sheath configured to enclose a proximal end of an implantable medical electrical lead, the proximal end of the lead including a terminal pin and a portion of a lead projecting from a distal end of the terminal pin. The protective sheath includes a tubular body forming a lumen extending from a proximal end to a distal end of the tubular body. The lumen has a diameter of about 0.2 mm to about 8.3 mm. The lumen is open at the distal end of the tubular body. The tubular body includes a proximal section and a distal section. The proximal section is adjacent to the proximal end of the tubular body and configured to enclose within the lumen a proximal end of the terminal pin. The distal section extends from the proximal section to the distal end of the tubular body. The distal section is configurable between an undeployed state wherein the distal section encloses within the lumen at least a portion of the terminal pin distal from the proximal end of the terminal pin, and a deployed state wherein the distal section encloses within the lumen the portion of the terminal pin distal from the proximal end of the terminal pin and the portion of the lead projecting from the distal end of the terminal pin.

Example 17 is the protective sheath of Example 16, wherein the lumen is closed at the proximal end of the tubular body.

Example 18 is the protective sheath of Example 16, wherein the lumen is open at the proximal end of the tubular body and the proximal section is further configured to project proximally past the proximal end of the terminal pin.

Example 19 is the protective sheath of Example 16, further including a tab projecting from the tubular body at the distal end of the tubular body.

Example 20 is the protective sheath of Example 16, wherein in the undeployed state, at least a portion of the distal section is folded by doubling the tubular body back upon itself, and in the deployed state at least a portion of the folded distal section is unfolded.

Example 21 is the protective sheath of Example 16, wherein the lumen at the distal end of the tubular body is configured to enclose a proximal end of an introducer sheath hub.

Example 22 is the protective sheath of Example 21, wherein the diameter of the lumen increases from the proximal end of the tubular body to the distal end of the tubular body.

Example 23 is the protective sheath of Example 16, wherein the tubular body is formed of a flexible, non-conductive biocompatible material that is impervious to bacteria.

Example 24 is an introducer sheath assembly including an introducer sheath and a protective sheath. The introducer sheath includes a hub having a proximal end and a distal end, and a tubular sheath projecting from the distal end of the hub. The protective sheath has a proximal end and a distal end. The distal end of the protective sheath is attached to the hub adjacent to the proximal end of the hub. The protective sheath is configurable between an undeployed state wherein the proximal end of the protective sheath is adjacent to the hub and a deployed state wherein the proximal end of the protective sheath is away from the hub.

Example 25 is the introducer sheath assembly of Example 24, further including a tab projecting from the protective sheath at the proximal end of the protective sheath.

Example 26 is the introducer sheath assembly of Example 24, wherein in the undeployed state, at least a portion of the protective sheath is folded by doubling the protective sheath back upon itself, and in the deployed state the protective sheath is unfolded.

Example 27 is the introducer sheath assembly of Example 24, wherein a diameter of the protective sheath in the deployed state is constant along its length.

Example 28 is the introducer sheath assembly of Example 24, wherein the protective sheath is formed of a flexible, non-conductive biocompatible material that is impervious to bacteria.

Example 29 is the introducer sheath assembly of Example 24, wherein the protective sheath is attached to the hub by a lap joint.

Example 30 is the introducer sheath assembly of Example 24, wherein the protective sheath includes a scored portion adjacent to the hub.

Example 31 is a method of protecting a proximal end of an implantable medical electrical lead from bacterial contamination while a distal end of the implantable medical electrical lead is implanted within a patient, the proximal end of the implantable medical electrical lead projecting from a proximal end of a hub of an introducer sheath. The method includes gripping a proximal end of an undeployed protective sheath attached to the proximal end of the hub by a distal end of the protective sheath, and deploying the protective sheath around the proximal end of the implantable medical electrical lead by pulling the proximal end of the protective sheath away from the hub until the proximal end of the protective sheath extends past the proximal end of the implantable medical electrical lead.

Example 32 is the method of Example 31, wherein before deploying, at least a portion of the protective sheath is folded by doubling the protective sheath back upon itself, and deploying the protective sheath unfolds the protective sheath.

Example 33 is the method of Example 31, wherein gripping the proximal end of the undeployed protective sheath includes gripping a tab projecting from the proximal end of the protective sheath, and deploying the protective sheath includes pulling the tab past the proximal end of the implantable medical electrical lead.

Example 34 is the method of Example 31, further including detaching the distal end of the protective sheath from the hub, and pulling the protective sheath from of the proximal end of the implantable medical electrical lead before removing the introducer sheath.

Example 35 is the method of Example 34, wherein detaching the distal end of the protective sheath includes tearing the protective sheath along a scored portion of the protective sheath adjacent to the hub.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 7A and 7B are perspective views of a protective sheath configured to enclose the proximal end of an implantable medical electrical lead, according to embodiments of the disclosure.

FIGS. 8A and 8B are perspective views of an introducer sheath assembly including a protective sheath configured to enclose the proximal end of an implantable medical electrical lead, according to embodiments of the disclosure.

Figure 1:
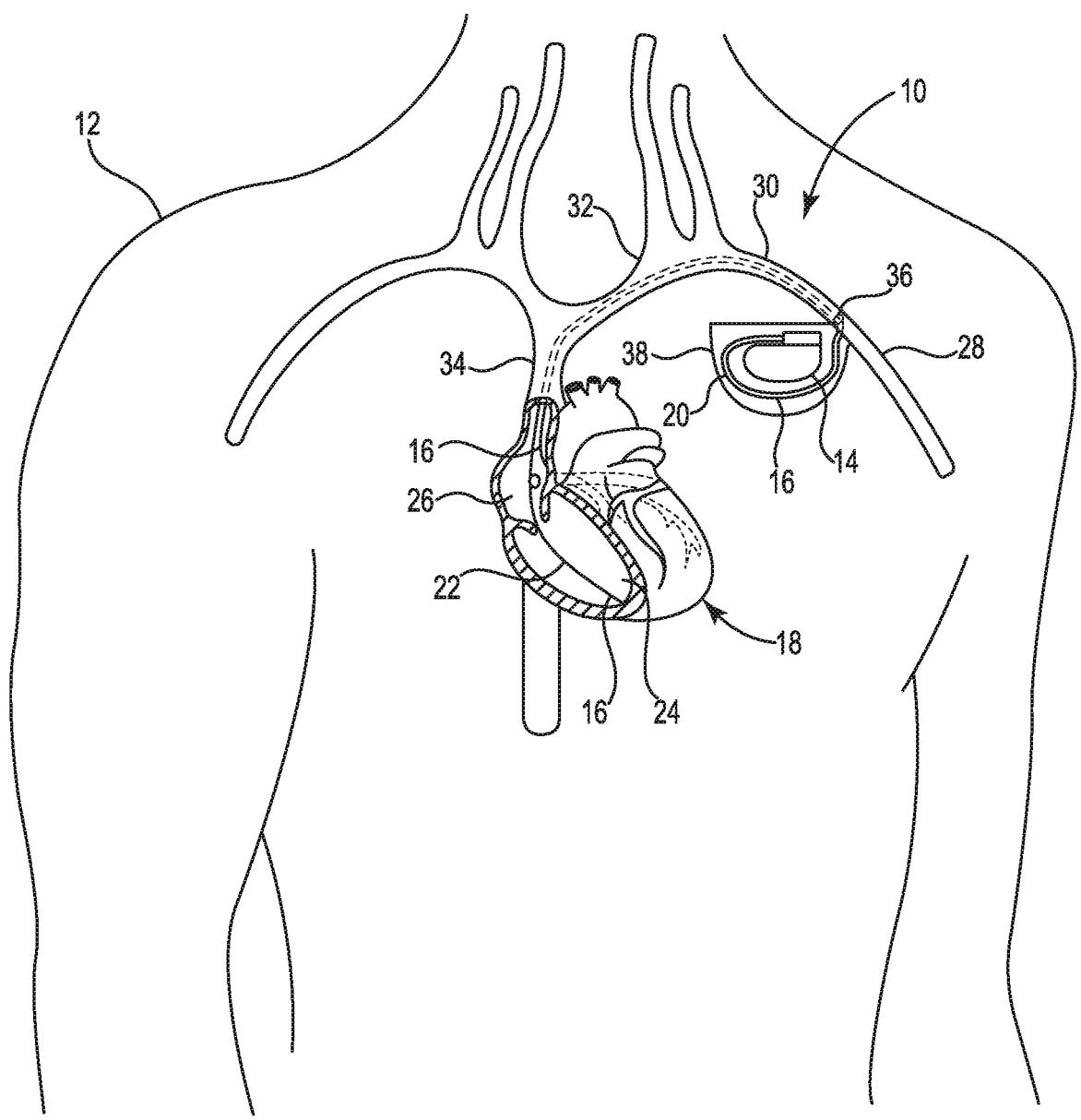
FIG. 1 is a schematic view of an implantable medical device in the form of a cardiac rhythm management system implanted in a patient, in accordance with embodiments of the disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Implanted pulse generators, or similar devices attached to electrical leads and implanted in a subcutaneous pocket, may need to be replaced at a later date, due to, for example, depletion of a battery powering the device. During replacement, the subcutaneous pocket is opened up, the pulse generator is removed from the pocket, and the leads are disconnected from the pulse generator. During replacement of the pulse generator, the disconnected lead ends including terminal pins may be laid down on operating spaces and moved around. Bacteria may be picked up by the lead ends during this time and enter the subcutaneous pocket as the lead ends are attached to a replacement pulse generator and inserted back into the subcutaneous pocket along with the replacement pulse generator.

Some embodiments of this disclosure include a protective sheath configured, as described below, to enclose the disconnected lead ends including terminal pins of an implantable medical electrical lead. The protective sheath can be formed of a material that is substantially impervious to bacteria. By enclosing the disconnected lead ends after they are disconnected form the pulse generator and removing the protective sheath just before they are connected to the replacement pulse generator and inserted into the subcutaneous pocket, bacteria may be prevented from being picked up by the leads ends and entering the subcutaneous pocket along with the lead ends.

During the subcutaneous implantation of implantable medical device electrical leads as described above, the unattached lead end including the terminal pin projects from the introducer sheath. The unattached lead end including a terminal pin may be laid down on operating spaces and moved around. Bacteria may be picked up by the lead end during this time and enter the subcutaneous pocket after the introducer sheath is extracted from the patient and the lead end is inserted into the subcutaneous pocket along with, for example, the pulse generator.

Some embodiments of this disclosure include an introducer sheath assembly including a protective sheath attached to an introducer sheath. The protective sheath can be deployed around the unattached lead end. By deploying the protective sheath, which is substantially impervious to bacteria, around the lead end until the introducer sheath is extracted from the patient, bacteria may be prevented from being picked up by the leads end and entering the subcutaneous pocket along with the lead end.

Preventing bacteria from entering the subcutaneous pocket by being carried on the lead end may reduce the incidence and/or severity of subcutaneous pocket infections associated with implanting or replacing implantable medical devices.

FIG. 1 is a schematic view of an implantable medical device (IMD) 10 in the form of a cardiac rhythm management system implanted in a patient 12. As shown in FIG. 1, the IMD 10 may include pulse generator 14 and a plurality of leads 16 (two shown) connecting the pulse generator 14 with treatment sites within a heart 18. Each of the plurality of leads 16 includes a proximal end 20 and a distal end 22. The pulse generator 14 may include electronic circuitry (not shown) and a battery (not shown). Each of the leads 16 may include conductors and electrodes (not shown) as necessary to convey electrical pulses and signals between the pulse generator 14 and the heart 18. As shown in FIG. 1, the heart 18 includes a right ventricle 24 and a right atrium 26. A major series of veins supplying blood to the heart 18 includes a left auxiliary vein 28, which flows into a left subclavian vein 30, which flows into a left brachiocephalic vein 32. The left brachiocephalic vein 32 flows into a superior vena cava 34, which supplies blood to the right atrium 26.

As further shown in FIG. 1, the leads 16 may enter the vascular system through a vascular entry site 36. In some embodiments, the vascular entry site 36 may be formed in a wall of the left auxiliary vein 28. In other embodiments, the vascular entry site 36 may be formed in a wall of the left subclavian vein 30. The leads 16 may extend from the left auxiliary vein 28, through the left subclavian vein 30, the left brachiocephalic vein 32, and the superior vena cava 34 to the heart 18. Within the heart 18, one of the leads 16 may be implanted in the right ventricle 24 and another of the leads 16 may be implanted in the right atrium 26. Thus, the right ventricle 24 and the right atrium 26 are treatment sites within the heart 18 that receive therapy from IMD 10 in the form of electrical pulses conveyed from the pulse generator 14 by way of the leads 16.

The pulse generator 14 may be implanted in a subcutaneous pocket 38 in the patient's chest, as shown in FIG. 1, for example. The proximal end 20 of each of the leads 16 extends from the pulse generator 14 to the vascular entry site 36 and may also be located within the subcutaneous pocket 38. Any excess length of the leads 16 may be coiled about the pulse generator 14 within the subcutaneous pocket 38.

Although FIG. 1 illustrates the IMD 10 in the form of a subcutaneously-implanted pulse generator and lead system, embodiments described herein can be employed with any implantable medical device implanted in a subcutaneous pocket for sensing intrinsic physiological electrical activity, delivering a therapeutic stimulus to patient tissue, or providing other therapy to specific treatment sites. For example, embodiments may be employed with a subcutaneously-implanted implantable cardioverter-defibrillator (ICD) housing and lead system. Such a system may include a housing implanted in a subcutaneous pocket in a patient's chest, and a lead traversing a subcutaneous path from the subcutaneous pocket to the anterior precordial region. Embodiments may be employed other implantable medical devices including, without limitation, cardioverter-defibrillator or cardiac resynchronization therapy devices, endocardial leads, epicardial leads, and neurostimulation systems such as spinal cord stimulation or deep brain stimulation device housings and associated leads, to name a few.

Figure 2:
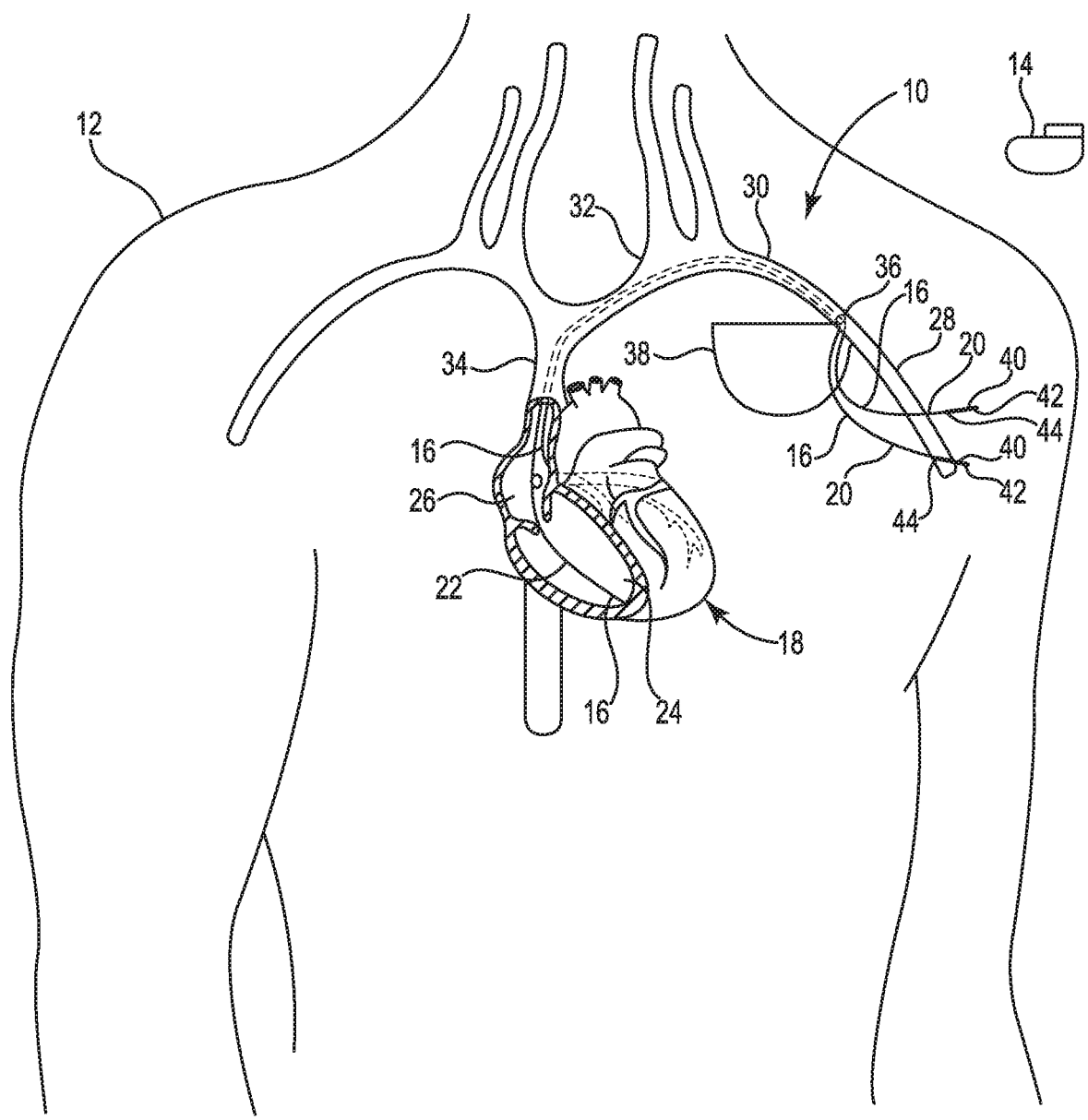
FIG. 2 is a schematic view of the implantable medical device of FIG. 1 during replacement of a pulse generator, in accordance with embodiments of the disclosure.

FIG. 2 is a schematic view of an implantable medical device (IMD) 10 during replacement of the pulse generator 14. In FIG. 2, the pulse generator 14 is removed from the subcutaneous pocket 38 after the subcutaneous pocket is opened up and the leads 16 are disconnected from the pulse generator 14. As shown in FIG. 2, the proximal end 20 of each of the leads 16 includes a terminal pin 40. The terminal pin 40 includes a proximal end 42 and a distal end 44 from which the lead 16 extends. During replacement of the pulse generator 14, the proximal end 20 of the lead 16, including the terminal pin 40 and a portion of the lead 16 extending from the terminal pin 40, may be laid down on operating spaces and moved around. Bacteria may be picked up by the proximal end 20 of each of the leads 16 during this time and enter the subcutaneous pocket as the proximal end 20 of each of the leads 16 are attached to a replacement pulse generator 14 and inserted back into the subcutaneous pocket 38 along with the replacement pulse generator 14.

Figure 3:
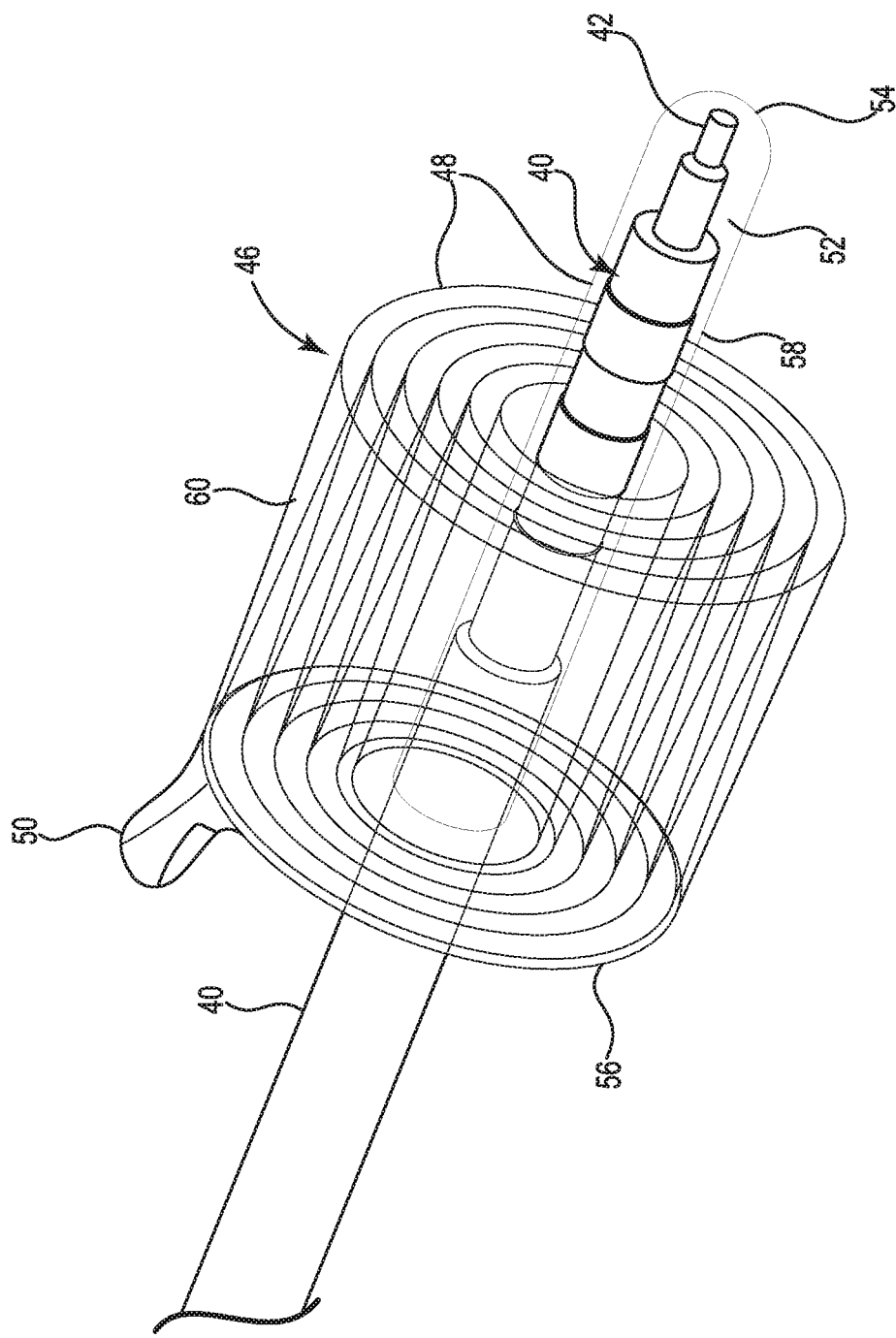
FIG. 3 is a perspective view of a protective sheath configured to enclose a proximal end of an implantable medical electrical lead, according to embodiments of the disclosure.
Figure 4A:
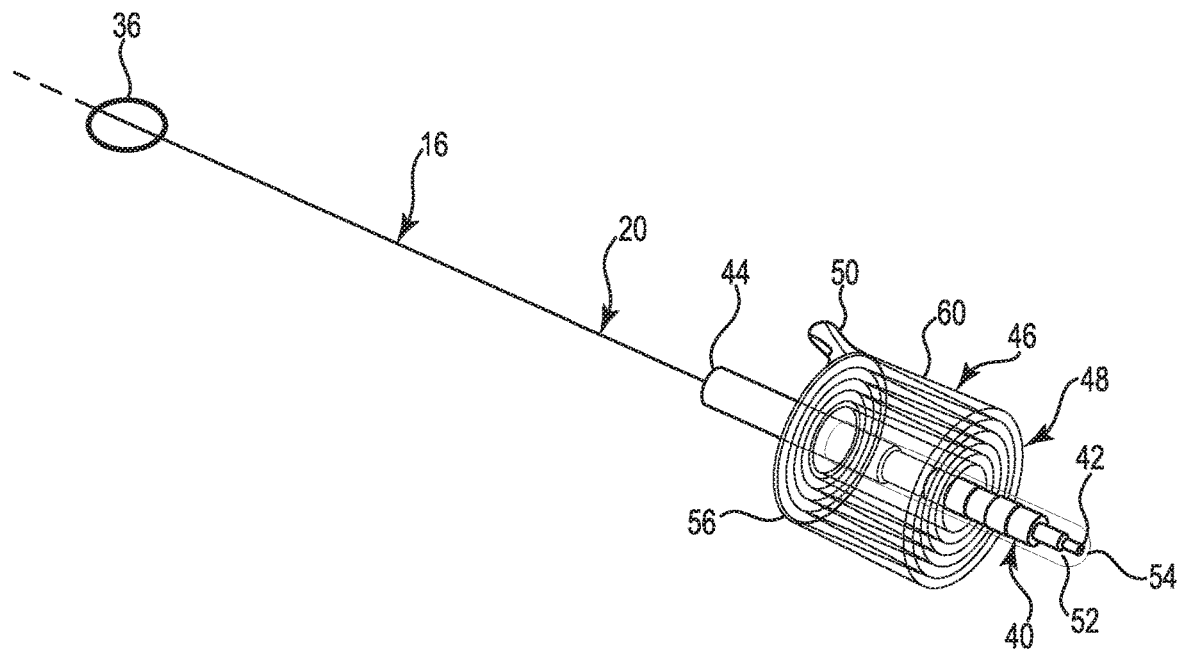
FIGS. 4A and 4B are perspective views of the protective sheath of FIG. 3 in undeployed and deployed states, in accordance with embodiments of the disclosure
Figure 4B:
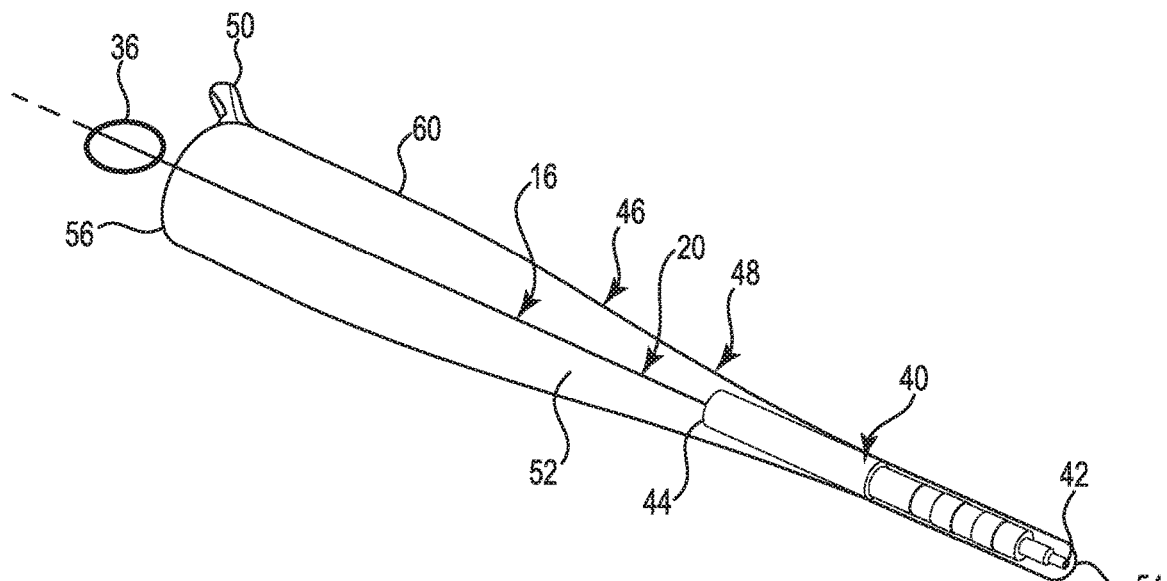

FIGS. 3, 4A and 4B are perspective views of a protective sheath 46 configured to enclose the proximal end 20 of the lead 16, according to embodiments of the disclosure. As shown in FIG. 3, the protective sheath 46 includes a tubular body 48 and, optionally, a tab 50. The tubular body 48 forms a lumen 52 extending from a proximal end 54 of the tubular body 48 to a distal end 56 of the tubular body 48. The tubular body 48 includes a proximal section 58 adjacent to the proximal end 54 of the tubular body 48 and a distal section 60 extending from the proximal section 58 to the distal end 56 of the tubular body 48. The proximal section 58 can be sized such that a portion of the lumen 52 along the proximal section 58 has a diameter larger than a diameter of the terminal pin 40. In this way, the proximal section 58 is configured to enclose within the lumen 52 the proximal end 42 of the terminal pin 40. The tab 50 projects from the tubular body 48 at the distal end 56 of the tubular body 48.

The distal section 60 is configurable between an undeployed state and a deployed state, as shown in FIGS. 4A and 4B, respectively. In the undeployed state shown in FIGS. 3 and 4A, the distal section 60 of the tubular body 48 encloses within the lumen 52 at least a portion of the terminal pin 40 distal from the proximal end 42 of the terminal pin 40. In the embodiment shown, in the undeployed state, at least a portion of the distal section 60 is folded by doubling the tubular body 48 back upon itself, as most clearly shown in FIG. 3. In the deployed state shown in FIG. 4B, the distal section 60 of the tubular body 48 encloses within the lumen 52 the portion of the terminal pin 40 distal from the proximal end 42 of the terminal pin 40 and the portion of the lead 16 extending from the distal end 44 of the terminal pin. In some embodiments, in the deployed state, the distal section 60 may enclose most of the proximal end 20 of the lead 16, nearly up to the vascular entry site 36 as shown in FIG. 4B.

In use, starting with the protective sheath 46 in the undeployed state as shown in FIG. 4A, the proximal section 58 of the tubular body 48 can be placed over the proximal end 42 of the terminal pin 40, and the proximal section 58 held in position by gripping the tubular body 48 against the terminal pin 40. The protective sheath 46 can be deployed by gripping the tab 50 at the distal end 56 of the tubular body 48 and pulling the distal end 56 along the lead 16 and away from the proximal end 54 of the tubular body 48. While the embodiment shown in FIGS. 3, 4A, and 4B includes the optional tab 50, in embodiments omitting the tab 50, the distal end 56 itself may be gripped instead. As the protective sheath 46 is deployed, the folded portions of the distal section 60 unfold until the tubular body 48 encloses the proximal end 20 of the lead 16 as shown in FIG. 4B. Once the protective sheath 46 is deployed, the tubular body 48 and the tab 50 can be released from being gripped.

The protective sheath 46 is configured, as described in reference to FIGS. 3, 4A, and 4B to enclose the disconnected proximal end 20 of the lead 16 including the terminal pin 40 after the proximal end 20 is disconnected from the pulse generator 14. The protective sheath 46 can prevent bacteria from attaching to the lead 16 when the lead 16 is be laid down on operating spaces and moved around. When the lead 16 is to be connected to a replacement pulse generator 14, the protective sheath 46 can be removed from the proximal end 20 and the lead 16 inserted into the subcutaneous pocket 38 (FIG. 2).

Figure 5:
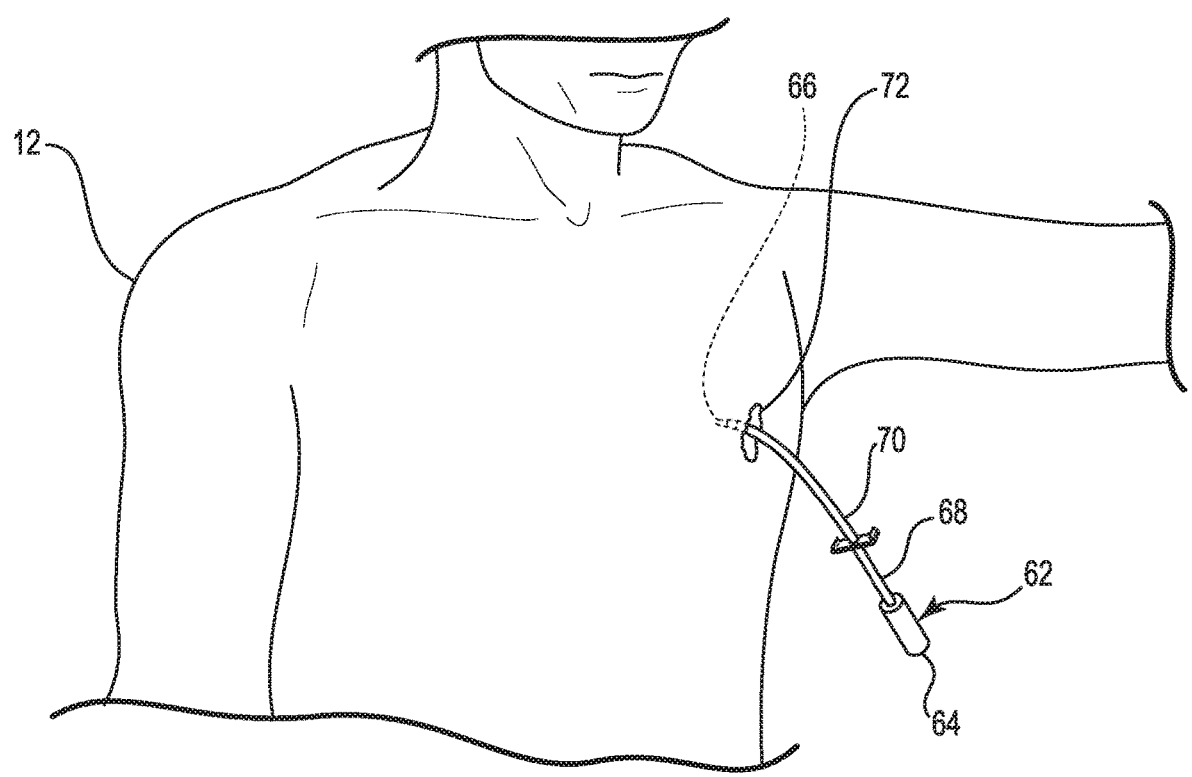
FIGS. 5 and 6 are schematic views illustrating the use of a tunneling tool to implant a medical electrical lead in a patient, in accordance with embodiments of the disclosure.
Figure 6:
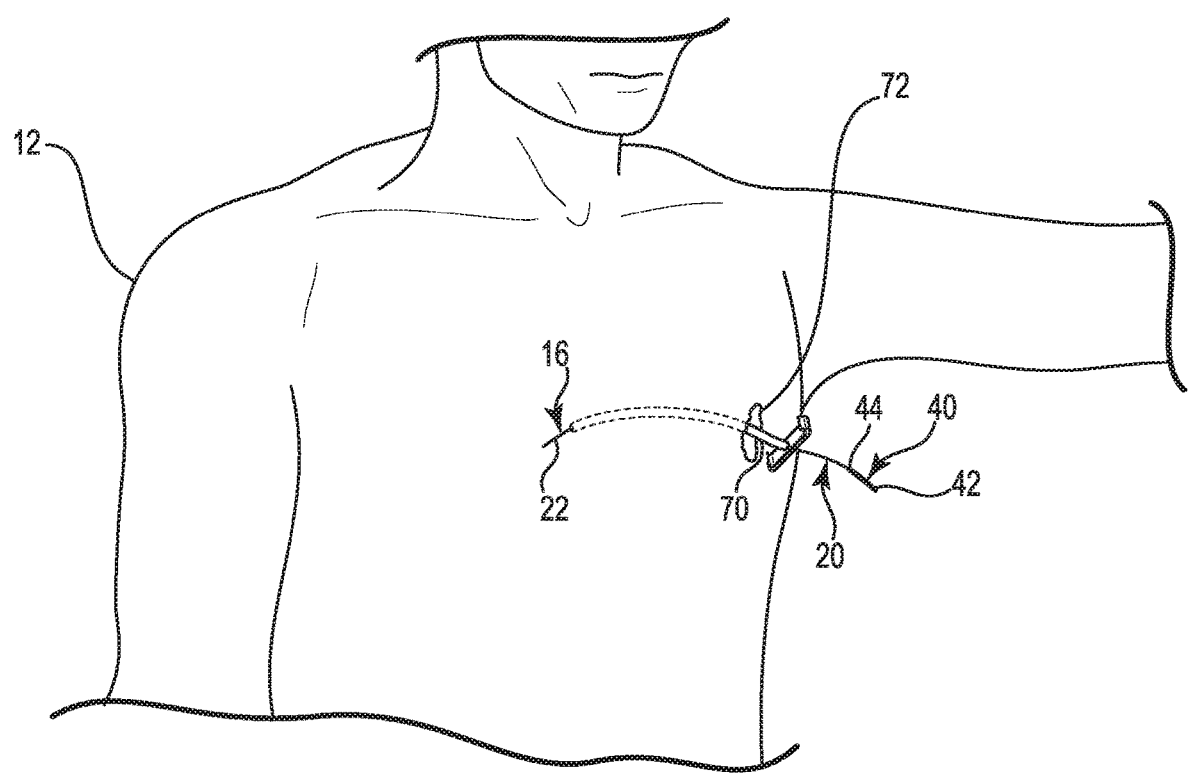

FIGS. 1-4B illustrated the use of the protective sheath 46 when replacing the pulse generator 14, according to some embodiments. FIGS. 5 and 6 are schematic views illustrating the use of a tunneling tool 62 to implant the lead 16 in the patient 12. As shown in FIG. 5, the tunneling tool 62 with a proximal end 64 and a distal end 66 includes an elongated tunneling rod or stylet 68 and an introducer sheath 70. The introducer sheath 70 may be a splitable or peelable type of introducer sheath, as is known in the art. The tunneling rod 68 extends through a lumen of the introducer sheath 70 such that a distal tip of the tunneling rod 68 projects from the lumen of the introducer sheath 70 to define the distal end 66 of the tunneling tool 62. As shown in FIG. 5, the distal end 66 of the tunneling tool 62 is inserted into an incision 72 made into the patient 12 at a suitable location. The incision 72 is an opening through which the tunneling tool 62 is inserted subcutaneously into the patient 12.

As shown in FIG. 6, after the distal end 66 of the tunneling tool 62 is inserted into the incision 72, the distal end 66 of the tunneling tool 62 is driven to a location within the patient 12 corresponding to a desired placement of the lead 16 to form a tunnel to the location. Once the desired location is reached, the tunneling rod 68 may be withdrawn from the introducer sheath 70, leaving a tunnel to the location by way of the lumen of the introducer sheath 70. Once the tunnel is formed, the distal end 22 of the lead 16 is inserted into the lumen of the introducer sheath 70 until the distal end 22 is at the desired location, leaving the proximal end 20 projecting from a proximal end of the introducer sheath 70. The proximal end 20 may be laid down on operating spaces and moved around. Bacteria may be picked up by the proximal end 20 of the lead 16 during this time and enter the subcutaneous pocket 38 (FIG. 1) when the proximal end 20 of the lead 16 is attached to the pulse generator 14 (FIG. 1) and inserted into the subcutaneous pocket 38 along with the pulse generator 14.

FIGS. 7A and 7B are perspective views of a protective sheath 74 configured to enclose the proximal end 20 of the lead 16 when the proximal end 20 projects from the proximal end of the introducer sheath 70, according to embodiments of the disclosure. As shown in FIGS. 7A and 7B, the introducer sheath 70 can include a hub 76 having a proximal end 78 and a distal end 80, and a tubular sheath 82 projecting from the distal end 80 of the hub 76. The protective sheath 74 is substantially the same as the protective sheath 46 described above in reference to FIG. 3, except that the lumen 52 at the distal end 56 of the tubular body 48 has a diameter larger than a diameter of the proximal end 78 and is thus configured to enclose the proximal end 78 of the hub 76. Thus, in the deployed state, the distal section 60 may enclose the proximal end 20 of the lead 16 and enclose the proximal end 78 of the hub 76.

In use, starting with the protective sheath 74 in the undeployed state as shown in FIG. 7A, the proximal section 58 of the tubular body 48 can be placed over the proximal end 42 of the terminal pin 40, and the proximal section 58 held in position by gripping the tubular body 48 against the terminal pin 40. The protective sheath 74 can be deployed by gripping the tab 50 at the distal end 56 of the tubular body 48 and pulling the distal end 56 along the lead 16 and away from the proximal end 54 of the tubular body 48 and toward the hub 76. As the protective sheath 74 is deployed, the folded portions of the distal section 60 unfold until the tubular body 48 encloses the proximal end 20 of the lead 16 and encloses the proximal end 78 of the hub 76, as shown in FIG. 7B. Once the protective sheath 74 is deployed, the tubular body 48 and the tab 50 can be released from being gripped.

The protective sheath 74 is configured, as described in reference to FIGS. 7A and 7B, to enclose the proximal end 20 of the lead 16 and the proximal end 78 of the hub 76 after the distal end 22 of the lead 16 is inserted into the lumen of the introducer sheath 70. The protective sheath 74 can prevent bacteria from attaching to the lead 16 when the lead 16 is be laid down on operating spaces and moved around. When the lead 16 is to be connected to the pulse generator 14, the protective sheath 74 can be removed from the proximal end 20 and the lead 16 can be inserted into the subcutaneous pocket 38 along with the pulse generator 14.

In the embodiments shown in FIGS. 4B and 7B, the diameter of the lumen 52 increases from the proximal end 54 of the tubular body 48 to the distal end 56 of the tubular body 48. However, it is understood that embodiments include protective sheaths in which the diameter of the lumen 52 is substantially constant along its length.

In the embodiments shown in FIGS. 3, 4A, 4B, 7A and 7B, the lumen 52 is closed at the proximal end 54 of the tubular body 48. In other embodiments, the lumen 52 can be open at the proximal end 54, and the proximal section 58 of the tubular body 48 projects proximally past the proximal end 42 of the terminal pin 40 to enclose the proximal end 20 of the lead 16.

FIGS. 8A and 8B illustrate another embodiment for preventing bacteria from attaching to the lead 16 when the proximal end 20 projects from the proximal end of the introducer sheath 70. FIGS. 8A and 8B are perspective views of an introducer sheath assembly 84 including the introducer sheath 70, a protective sheath 86 and, optionally, a tab 88. The protective sheath 86 includes a proximal end 90 and a distal end 92. The protective sheath 86 can have tubular structure open at both proximal end 90 and a distal end 92. The tab 88 projects from the protective sheath 86 at the proximal end 90. The distal end 92 is attached to the hub 76 adjacent to the proximal end 78 of the hub 76.

In the embodiment shown, the open distal end 92 of the protective sheath 86 surrounds and overlaps the proximal end 78 of the hub 76, forming a lap joint. In other embodiments, the distal end 92 may form a butt joint with the proximal end 78 of the hub 76. In some embodiments, the protective sheath 86 may be attached to the hub 76 by an adhesive, tape, or a mechanical fastening device, for example, a clamp. In other embodiments, the protective sheath 86 is attached to the hub 76 by a compression fit between the protective sheath 86 around the hub 76. A hoop stress produced by the distal end 92 of the protective sheath 86 around the hub 76 is sufficient to hold the protective sheath 86 against the hub 76 such that the distal end 92 cannot be easily detached from the hub 76.

The protective sheath 86 is configurable between an undeployed state and a deployed state, as shown in FIGS. 8A and 8B, respectively. In the undeployed state, at least a portion of the protective sheath 86 is folded by doubling the protective sheath 86 back upon itself, as shown in FIG. 8A (and similarly to the protective sheath 46 shown most clearly in FIG. 3) such that the proximal end 90 of the protective sheath 86 is adjacent to the hub 76, but still proximal to the distal end 92 of the protective sheath. In the deployed state shown in FIG. 8B, the proximal end 90 of the protective sheath 86 is away from the hub 76 and the protective sheath 86 is unfolded. In the deployed state, the protective sheath 86 encloses the proximal end 20 of the lead 16, including the terminal pin 40.

In use, starting with the protective sheath 86 in the undeployed state as shown in FIG. 8A, the protective sheath 86 can be deployed around the proximal end 20 of the lead 16 by gripping the tab 88 at the proximal end 90 of the protective sheath 86 and pulling the proximal end 90 along the lead 16 and away from the hub 76 and toward the terminal pin 40. While the embodiment shown in FIGS. 7A and 7B includes the optional tab 88, in embodiments omitting the tab 88, the proximal end 90 itself may be gripped instead. As the protective sheath 86 is deployed, the folded portions of the protective sheath 86 unfold until the protective sheath 86 encloses the proximal end 20 of the lead 16 and extends past the proximal end 20, as shown in FIG. 8B. Once the protective sheath 86 is deployed, the tab 88 can be released from being gripped.

The protective sheath 86 is configured, as described in reference to FIGS. 8A and 8B, to enclose the proximal end 20 of the lead 16 after the distal end 22 of the lead 16 is inserted into the lumen of the introducer sheath 70. The protective sheath 86 can prevent bacteria from attaching to the lead 16 when the lead 16 is be laid down on operating spaces and moved around.

When the lead 16 is to be connected to the pulse generator 14, the protective sheath 86 can be removed from the proximal end 20 and the lead 16 can be inserted into the subcutaneous pocket 38 along with the pulse generator 14. In some embodiments, the protective sheath 86 may include a circumferentially scored portion 94 adjacent to and proximal of the proximal end 78 of the hub 76 so that the protective sheath 86 can be detached from the hub 76 by tearing along the circumferentially scored portion 94, and removed from the proximal end 20 of the lead 16. In embodiments in which the introducer sheath 70 is a splitable or peelable sheath, the protective sheath 86 may include a pull tab 96 connected to at least one scored portion 98 (two shown in FIG. 8B) at the distal end 92 adjacent to the hub 76. Pulling the pull tab 96 tears the protective sheath 86 along the scored portion 98, separating portions of the protective sheath 86 on either side of the at least one scored portion 98 to relieve the hoop stress produced by the distal end 92 of the protective sheath 86 around the hub 76. With the hoop stress relieved, the protective sheath 86 can be detached from the hub 76 and removed from the proximal end 20 of the lead 16 so that the introducer sheath 70 may be split without interference from the protective sheath 86 and removed from the patient 12 after the lead 16 is in its final location.

In the embodiment shown in FIG. 8B, a diameter of the protective sheath 86 is substantially constant along its length. However, it is understood that embodiments include the protective sheath 86 in which the diameter is not constant along its length.

The protective sheaths 46, 74, and 86 described above can be formed of a flexible material that is biocompatible and substantially impervious to bacteria. The material may be impervious to bacteria by being non-porous, or by having pores small enough to prevent the movement of bacteria through the material. In some embodiments, the material may also be non-conductive to inhibit the flow of stray voltages into the body resulting from the contact with charged surfaces the operating space and to insulate the terminal pin from stray voltage inputs. Suitable materials include, for example, polyurethane, silicone, polytetrafluoroethylene (PTFE), expanded polytetrafluoroethylene (EPTFE), acrylonitrile butadiene rubber, and tightly-woven cloths made of any of the preceding materials. The material may be clear, translucent, or opaque.

Embodiments of the protective sheaths 46, 74, and 86 described above can have diameters as small as about 0.2 mm, about 0.5 mm, about 1 mm, or about 2 mm, or as large as about 4 mm, about 5 mm, about 6 mm, or about 8.3 mm, or within any range defined between any pair of the foregoing values. In some embodiments, the protective sheath diameter can range from about 0.2 mm to about 8.3 mm, from about 0.5 mm to about 6 mm, from about 1 mm to about 5 mm, or from about 2 mm to about 4 mm. In some embodiments, the protective sheath diameter can be about 3 mm.

Embodiments of the protective sheaths 46, 74, and 86 described above can have lengths as small as about 25 mm, about 45 mm, about 65 mm, or about 130 mm, or as great as about 250 mm, about 500 mm, about 1000 mm, or about 1500 mm, or within any range defined between any pair of the foregoing values. In some embodiments, the protective sheath length can range from about 25 mm to about 1500 mm, from about 045 mm to about 1000 mm, from about 65 mm to about 500 mm, or from about 130 mm to about 250 mm. In some embodiments, the protective sheath diameter can be about 190 mm.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A protective sheath configured to enclose a proximal end of an implantable medical electrical lead, the proximal end of the lead including a terminal pin and a portion of a lead projecting from a distal end of the terminal pin, the protective sheath comprising:
   a tubular body forming a lumen extending from a proximal end to a distal end of the tubular body, the lumen having a diameter of about 0.2 mm to about 8.3 mm, the lumen open at the distal end of the tubular body, the tubular body including:
      a proximal section adjacent to the proximal end of the tubular body and configured to enclose within the lumen a proximal end of the terminal pin; and
      a distal section extending from the proximal section to the distal end of the tubular body, the distal section configurable between:
         an undeployed state wherein the distal section encloses within the lumen at least a portion of the terminal pin distal from the proximal end of the terminal pin; and
         a deployed state wherein the distal section encloses within the lumen the portion of the terminal pin distal from the proximal end of the terminal pin and the portion of the lead projecting from the distal end of the terminal pin.

2. The protective sheath of claim 1, wherein the lumen is closed at the proximal end of the tubular body.

3. The protective sheath of claim 1, wherein the lumen is open at the proximal end of the tubular body and the proximal section is further configured to project proximally past the proximal end of the terminal pin.

4. The protective sheath of claim 1, further including a tab projecting from the tubular body at the distal end of the tubular body.

5. The protective sheath of claim 1, wherein in the undeployed state, at least a portion of the distal section is folded by doubling the tubular body back upon itself, and in the deployed state at least a portion of the folded distal section is unfolded.

6. The protective sheath of claim 1, wherein the lumen at the distal end of the tubular body is configured to enclose a proximal end of an introducer sheath hub.

7. The protective sheath of claim 6, wherein the diameter of the lumen increases from the proximal end of the tubular body to the distal end of the tubular body.

8. The protective sheath of claim 1, wherein the tubular body is formed of a flexible, non-conductive biocompatible material that is impervious to bacteria.

9. An introducer sheath assembly comprising:
   an introducer sheath including:
      a hub having a proximal end and a distal end; and
      a tubular sheath projecting from the distal end of the hub; and
   a protective sheath having a proximal end and a distal end, the distal end of the protective sheath attached to the hub adjacent to the proximal end of the hub, the protective sheath configurable between an undeployed state wherein the proximal end of the protective sheath is adjacent to the hub and a deployed state wherein the proximal end of the protective sheath is away from the hub.

10. The introducer sheath assembly of claim 9, further including a tab projecting from the protective sheath at the proximal end of the protective sheath.

11. The introducer sheath assembly of claim 9, wherein in the undeployed state, at least a portion of the protective sheath is folded by doubling the protective sheath back upon itself, and in the deployed state the protective sheath is unfolded.

12. The introducer sheath assembly of claim 9, wherein a diameter of the protective sheath in the deployed state is constant along its length.

13. The introducer sheath assembly of claim 9, wherein the protective sheath is formed of a flexible, non-conductive biocompatible material that is impervious to bacteria.

14. The introducer sheath assembly of claim 9, wherein the protective sheath is attached to the hub by a lap joint.

15. The introducer sheath assembly of claim 9, wherein the protective sheath includes a scored portion adjacent to the hub.

16. A method of protecting a proximal end of an implantable medical electrical lead from bacterial contamination while a distal end of the implantable medical electrical lead is implanted within a patient, the proximal end of the implantable medical electrical lead projecting from a proximal end of a hub of an introducer sheath, the method comprising:
   gripping a proximal end of an undeployed protective sheath attached to the proximal end of the hub by a distal end of the protective sheath; and
   deploying the protective sheath around the proximal end of the implantable medical electrical lead by pulling the proximal end of the protective sheath away from the hub until the proximal end of the protective sheath extends past the proximal end of the implantable medical electrical lead.

17. The method of claim 16, wherein before deploying, at least a portion of the protective sheath is folded by doubling the protective sheath back upon itself, and deploying the protective sheath unfolds the protective sheath.

18. The method of claim 16, wherein gripping the proximal end of the undeployed protective sheath includes gripping a tab projecting from the proximal end of the protective sheath, and deploying the protective sheath includes pulling the tab past the proximal end of the implantable medical electrical lead.

19. The method of claim 16, further comprising:
   detaching the distal end of the protective sheath from the hub; and
   pulling the protective sheath from of the proximal end of the implantable medical electrical lead before removing the introducer sheath.

20. The method of claim 19, wherein detaching the distal end of the protective sheath includes tearing the protective sheath along a scored portion of the protective sheath adjacent to the hub.

* * * * *